United States Patent
Xu et al.

(10) Patent No.: US 10,392,318 B2
(45) Date of Patent: Aug. 27, 2019

(54) MODIFIED COMPOSITE MOLECULAR SIEVE AND PREPARATION METHOD THEREOF, AND PARAFFIN ISOMERIZATION CATALYST

(71) Applicants: China Petroleum & Chemical Corporation, Beijing (CN); Fushun Research Institute of Petroleum and Petrochemicals, SINOPEC CORP., Fushun, Liaoning (CN)

(72) Inventors: Huiqing Xu, Liaoning (CN); Quanjie Liu, Liaoning (CN); Liming Jia, Liaoning (CN); Wei Wang, Liaoning (CN)

(73) Assignees: CHINA PETROLEUM & CHEMICAL CORPORATION, Beijing (CN); FUSHUN RESEARCH INSTITUTE OF PETROLEUM AND PETROCHEMICALS, SINOPEC CORP., Fushun, Liaoning (CN)

( * ) Notice: Subject to any disclaimer, the term of this patent is extended or adjusted under 35 U.S.C. 154(b) by 162 days.

(21) Appl. No.: 15/347,166

(22) Filed: Nov. 9, 2016

(65) Prior Publication Data

US 2017/0129829 A1    May 11, 2017

(30) Foreign Application Priority Data

Nov. 9, 2015 (CN) .......................... 2015 1 0751186
Nov. 9, 2015 (CN) .......................... 2015 1 0751279

(51) Int. Cl.
*B01J 29/06* (2006.01)
*C07C 5/27* (2006.01)
(Continued)

(52) U.S. Cl.
CPC ........... *C07C 5/2775* (2013.01); *B01J 29/708* (2013.01); *B01J 29/7046* (2013.01); *B01J 29/7088* (2013.01); *B01J 29/7092* (2013.01); *B01J 29/7096* (2013.01); *B01J 29/7461* (2013.01); *B01J 29/7476* (2013.01); *B01J 29/7484* (2013.01); *B01J 29/7492* (2013.01); *B01J 29/7861* (2013.01); *B01J 29/7876* (2013.01); *B01J 29/7884* (2013.01); *B01J 29/7892* (2013.01); *B01J 29/80* (2013.01); *B01J 35/0006* (2013.01); *B01J 35/1019* (2013.01); *B01J 35/1038* (2013.01); *B01J 35/1042* (2013.01); *B01J 37/0219* (2013.01); *B01J 37/10* (2013.01); *C07C 5/2708* (2013.01); *C10G 45/64* (2013.01);
(Continued)

(58) Field of Classification Search
CPC B01J 29/7861; B01J 29/7876; B01J 29/7884; B01J 29/7892; B01J 29/7461; B01J 29/7476; B01J 29/7484; B01J 29/7492; B01J 29/7042; B01J 29/7046; B01J 29/703; B01J 29/7038; B01J 29/708; B01J 29/7088; B01J 29/7092; B01J 29/7096; B01J 2229/186; B01J 29/80; B01J 2229/42; B01J 35/0006; B01J 35/1019; B01J 35/1038; B01J 35/1042; B01J 37/10; B01J 37/0219; C07C 2529/70; C07C 2529/74; C07C 2529/76; C07C 2529/78; C07C 2529/80
USPC ...................... 502/60, 63, 64, 66, 67, 69, 71
See application file for complete search history.

(56) References Cited

U.S. PATENT DOCUMENTS

| | | |
|---|---|---|
| 4,247,388 A | 1/1981 | Banta et al. |
| 4,419,420 A | 12/1983 | Ishizaki |

(Continued)

FOREIGN PATENT DOCUMENTS

| | | |
|---|---|---|
| CN | 103361116 A | 10/2013 |
| CN | 104549462 A | 4/2015 |

(Continued)

OTHER PUBLICATIONS

Xu Huiqing et al., Machine translation of CN104549461A, Apr. 2015.*

(Continued)

*Primary Examiner* — Elizabeth D Wood
(74) *Attorney, Agent, or Firm* — Novick, Kim & Lee, PLLC; Allen Xue

(57) ABSTRACT

The present invention provides a modified composite molecular sieve, and a preparation method and an application of the modified composite molecular sieve. The modified composite molecular sieve comprises $SiO_2$ and a composite molecular sieve that comprises molecular sieve MCM-22 and crystalline molecular sieve selected from at least one of ZSM-22, ZSM-23 and ZSM-48, wherein, the molecular sieve MCM-22 covers around the crystalline molecular sieve. The present invention further provides a catalyst and an application of the catalyst. The catalyst comprises a carrier and a noble metal loaded on the carrier, wherein, the carrier comprises a modified composite molecular sieve that is the modified composite molecular sieve provided in the present invention or the modified composite molecular sieve obtained with the method provided in the present invention. The catalyst that utilizes the composite molecular sieve as a carrier not only can decrease the solidifying point of waxy raw oil, but also can improve the yield of liquid product, is especially applicable to the isomerization dewaxing process of lube distillate, and has an advantage of remarkably improving the viscosity index of lube base oil.

20 Claims, 2 Drawing Sheets

(51) Int. Cl.
*B01J 29/78* (2006.01)
*B01J 29/74* (2006.01)
*B01J 29/70* (2006.01)
*B01J 35/00* (2006.01)
*B01J 35/10* (2006.01)
*B01J 37/10* (2006.01)
*B01J 37/02* (2006.01)
*B01J 29/80* (2006.01)
*C10G 45/64* (2006.01)

(52) U.S. Cl.
CPC .......... *B01J 29/703* (2013.01); *B01J 29/7038* (2013.01); *B01J 29/7042* (2013.01); *B01J 2229/186* (2013.01); *B01J 2229/42* (2013.01); *C07C 2529/70* (2013.01); *C07C 2529/74* (2013.01); *C07C 2529/76* (2013.01); *C07C 2529/78* (2013.01); *C07C 2529/80* (2013.01)

(56) References Cited

U.S. PATENT DOCUMENTS

| | | | |
|---|---|---|---|
| 4,518,485 A | 5/1985 | LaPierre et al. | |
| 4,599,162 A | 7/1986 | Yen | |
| 4,601,993 A | 7/1986 | Chu et al. | |
| 4,659,311 A | 4/1987 | Raskin | |
| 4,919,788 A | 4/1990 | Chen et al. | |
| 5,110,445 A | 5/1992 | Chen et al. | |
| 5,135,638 A | 8/1992 | Miller | |
| 5,149,421 A | 9/1992 | Miller | |
| 5,705,726 A * | 1/1998 | Abichandani | B01J 29/40 585/481 |
| 5,817,907 A | 10/1998 | Benazzi et al. | |
| 5,833,837 A | 11/1998 | Miller | |
| 5,990,371 A | 11/1999 | Martens et al. | |
| 6,204,426 B1 | 3/2001 | Miller et al. | |
| 6,504,074 B2 * | 1/2003 | Verduijn | B01J 29/80 502/67 |

FOREIGN PATENT DOCUMENTS

| | | |
|---|---|---|
| CN | 104556125 A | 4/2015 |
| JP | 5465822 B2 | 4/2014 |

OTHER PUBLICATIONS

Xiu-Bin Zhang et al., "Toluene disproportionation over ZSM-5 modified by silica deposition and hydrothermal reatment", Industrial Catalysis, Aug. 2005, vol. 13, No. 8, pp. 35-39.

* cited by examiner

MODIFIED COMPOSITE MOLECULAR SIEVE AND PREPARATION METHOD THEREOF, AND PARAFFIN ISOMERIZATION CATALYST

This application claims priority to Chinese Application No. 201510751186.9 filed on Nov. 9, 2015, titled "Paraffin Isomerization Catalyst and Preparation Method and Application Thereof" and Chinese Application No. 201510751279.1 filed on Nov. 9, 2015, titled "MCM-22/ZSM-22 Composite Molecular Sieve Catalyst and Preparation Method and Application Thereof", which are specifically and entirely incorporated by reference.

FIELD OF THE INVENTION

The present invention relates to a modified composite molecular sieve, a preparation method of the modified composite molecular sieve; and a catalyst of which the carrier comprises the modified composite molecular sieve; particularly, the present invention relates to a modified composite molecular sieve that comprises molecular sieve MCM-22, a preparation method of the modified composite molecular sieve, an paraffin isomerization catalyst of which the carrier comprises the modified composite molecular sieve.

BACKGROUND OF THE INVENTION

The isomerization reaction of n-alkanes is an important reaction in the petroleum processing process, such as the isomerization dewaxing process of lube oil and the isomerization visbreaking process of diesel oil. N-alkanes are non-ideal constituents in lube distillates, and may result in increased pour point and degraded low-temperature properties of the lube distillates. To improve those properties, the n-alkanes, which have high melting points, must be removed fully or partially. At present, common dewaxing methods mainly include solvent dewaxing, catalytic dewaxing, and isomerization dewaxing. Solvent dewaxing is to utilize the solubility of wax in a solvent to remove wax, but has the following drawbacks: it is difficult to choose an appropriate solvent, a large amount of organic solvent is wasted, the treatment process is harmful to human body and may pollute the environment, the equipment investment and operation costs are high, and the product quality is confined by the raw material. Catalytic dewaxing is to utilize a catalyst that has a shape-selective cracking function to carry out selective catalytic cracking of the wax constituent in the distillate, so that the wax constituent is cracked into hydrocarbons with smaller molecules. For example, in the U.S. Pat. No. 4,247,388, a catalytic dewaxing method is used to remove wax from lube oil. The drawbacks of the catalytic dewaxing method include: the base oil yield is low, the loss of viscosity index is severe, and the values of the byproducts are low, since a large quantity of high-value macromolecular compounds are converted into low-value substances with small molecules. Compared with the two dewaxing method described above, isomerization dewaxing is to make macromolecular wax have an isomerization reaction to generate isoalkanes, which have lower solidifying points and pour points and higher viscosity indexes than the wax that has the same molecular weight, and the isoalkanes still remain in the heavy distillate; thus, the yield of distillates is greatly improved.

Presently, there are many reports on isomerization dewaxing catalysts. For example, the U.S. Pat. Nos. 5,990,371, 5,833,837, 5,817,907, 5,149,421, 5,135,638, 5,110,445, 4,919,788, 4,419,420, 4,601,993, 4,599,162, and 4,518,485, etc. relate to isomerization dewaxing techniques. The acidic constituents used in those isomerization dewaxing techniques mainly include mordenite and molecular sieves SAPO-11, SAPO-31, SAPO-41, ZSM-23, SSZ-32 and ZSM-48. Molecular sieves different from each other in structure are suitable for different purposes, because they have unique pore canal structures and physical and chemical properties. Molecular sieve ZSM-5 has pore canals in three-dimensional ten-membered ring structure, molecular sieve NU-87 has pore canals in two-dimensional ten-membered ring structure, molecular sieves ZSM-22, EU-1 and SAPO-11 have pore canals in one-dimensional ten-membered ring structure, and molecular sieve MCM-22 has two separate multi-membered ring pore canal systems, wherein, one system has two-dimensional sinusoidal and crossed ten-membered ring pore canals. Those molecular sieves have their unique effects in isomerization reactions of hydrocarbon molecules. However, the effects are somewhat different from each other when those molecular sieves are used in isomerization dewaxing, owing to the slight differences in the pore canal structures and physical and chemical properties. All of those materials can make paraffinic hydrocarbons have isomerization reactions to some extent. However, for some reactions, e.g., reactions of lube distillate, the reactions are not always participated by the same molecules, because the constituents are complex. Therefore, molecular sieves that have a uniform structure may have some adaptive problems in those reactions. Consequently, a catalytic material that matches the molecules of one constituent well may be not ideal for other constituents. The n-alkanes in lube distillate and diesel oil result in degraded low-temperature fluidity of lube oil and diesel oil, owing to their high solidifying points. Isomerization dewaxing is to utilize a bi-functional catalyst with special pore structures to convert long-chain n-alkanes and polycyclic naphthenes that have high melting points in the wax constituent into isoalkanes with single branched chain and monocyclic naphthenes with long branched chains that have lower melting points. However, the melting point of the alkane will be increased if the isomerization degree is too high. Therefore, the isomerization degree of the wax molecules must be controlled appropriately. Hence, there is a strict requirement for the acidic property and pore structure of the acidic constituent and the hydrogenation constituent. Generally speaking, the acidic constituent(component) should have acid sites with moderate intensity and pore structures with space limitation function; in addition, the active metal constituent must have activity for rapid hydrogenation/dehydrogenation, so as to prevent further isomerization or even cracking of tertiary carbonium ions. Since the cracking reaction converts high-carbon alkanes into small-molecular low-carbon alkanes and thereby decreases the yield of the target product, the isomerization reaction should be promoted as far as possible, and the cracking reaction should be inhibited as far as possible. The patent document U.S. Pat. No. 6,204,426 has put forward a process for preparing an isomerization catalyst utilizing a mixture of SAPO-11, SAPO-31, SAPO-41, ZSM-48, ZSM-23 and ZSM-35, etc. as a carrier, and the patent document U.S. Pat. No. 5,833,837 has put forward a process for producing lube base oil with a dual-catalyst system, i.e., using SAPO-11, SAPO-31, and SAPO-41 series catalysts for isomerization of light lube oil constituents respectively, and using ZSM-5 catalyst for isomerization of heavy lube oil constituents. However, both of the processes have their drawbacks. Specifically, the former process can't give full play to the synergetic effect of the constituents of the mixed molecular sieve, and the latter process prolongs the process flow, increases operating difficulties, and severely increases the cost of investment.

CONTENTS OF THE INVENTION

To overcome the drawbacks in the prior art, the present invention provides a modified composite molecular sieve. A catalyst that utilizes the modified composite molecular sieve as a carrier not only can decrease the solidifying point of waxy raw oil, but also can improve the yield of liquid product, is especially applicable to the isomerization dewaxing process of lube distillate, and has an advantage of remarkably improve the viscosity index of lube base oil.

According to a first aspect of the present invention, the present invention provides a modified composite molecular sieve, which comprises $SiO_2$ and a composite molecular sieve that comprises molecular sieve MCM-22 and a crystalline molecular sieve, designated as "molecular sieve A," selected from at least one of molecular sieves ZSM-22, ZSM-23 and ZSM-48, wherein, the molecular sieve MCM-22 covers around the molecular sieve A, and the $SiO_2$ is loaded on the composite molecular sieve.

According to a second aspect of the present invention, the present invention provides a method for preparing a modified composite molecular sieve, comprising: loading an organic silicon source onto a composite molecular sieve optionally in the presence of solvent, and then treating in the presence of water vapor, and optionally drying and/or calcinating, wherein, the composite molecular sieve comprises molecular sieve MCM-22 and molecular sieve A selected from at least one of molecular sieves ZSM-22, ZSM-23 and ZSM-48, and the molecular sieve MCM-22 covers(or grows) around the molecular sieve A.

According to a third aspect of the present invention, the present invention provides an application of the modified composite molecular sieve as a catalyst carrier.

According to a fourth aspect of the present invention, the present invention provides a paraffin isomerization catalyst comprises a carrier and a noble metal loaded on the carrier, wherein, the carrier comprises a modified composite molecular sieve that is the modified composite molecular sieve provided in the present invention or the modified composite molecular sieve obtained with the method provided in the present invention.

According to a fifth aspect of the present invention, the present invention provides an application of the catalyst according to the present invention in paraffin isomerization.

Compared with the prior art, the present invention has the following advantages:
(1) The modified composite molecular sieve provided in the present invention is different from molecular sieve MCM-22 or a composite molecular sieve formed simply by mixing one or more of ZSM-22, ZSM-23, and ZSM-48 physically: the modified composite molecular sieve provided in the present invention has pore canal structure and acidity characteristics of the two types of molecular sieves, which is to say, the molecular sieve MCM-22 is "absorbed" on the surface of a molecular sieve that is effective for selective isomerization reaction of long and straight chain paraffin. Owing to the fact that the cross section of molecular sieve MCM-22 is a twelve-membered ring cylindrical super-cage with 0.71*0.71*0.91 nm free internal space, pockets with high adsorptive capacity can be formed on the external surface of the crystal, secondary channels are provided for the reactants while reactants that have branched chains are prevented from contacting with the active sites, and thereby the generation of multi-branched chain isomers is avoided; in addition, the occurrence of subsidiary reactions (e.g., cracking reaction) is inhibited and the isomerization selectivity is improved, while the catalyst is provided with an ideal long-chain paraffin isomerization function.

(2) The present invention employs a $SiO_2$ modified composite molecular sieve, which greatly improves isomerization selectivity; in a preferred embodiment of the present invention, an organic silicon source that has a large kinetic diameter, such as tetraethyl orthosilicate (molecular diameter>0.8 nm) is used as a modifier; owing to the high molecular volume, the organic silicon source not only can combine with hydroxy on the surface of the molecular sieve, but also can cover the acid sites in the "outer" molecular sieve catalyst purposely, to avoid the occurrence of non-selective cracking reaction at those sites; moreover, depending on the degree of silicon modification treatment, the active sites in the MCM-22 pore canals in the outer layer of the composite molecular sieve can be covered partially or fully, so that the reactants more likely contact with the pores of the molecular sieve A that has selectivity to long and straight chain paraffin; thus, the isomerization selectivity is further improved greatly;

(3) In a preferred embodiment of the present invention, the alkane isomerization catalyst utilizes molecular sieve MCM-22 and a modified composite molecular sieve that comprises one or more of molecular sieves ZSM-22, ZSM-23 and ZSM-48 at an appropriate mass ratio as a carrier partially or fully; the alkane isomerization catalyst has advantages such as high product yield, low pour point (solidifying point), and high viscosity index when it is used in hydroisomerization reaction of lube distillate;

(4) In a preferred embodiment of the present invention, an organic halogen compound is added in the composite molecular sieve preparation process, so that the molecular sieve MCM-22 can grow uniformly around the molecular sieve that comprises one or more of molecular sieves ZSM-22, ZSM-23 and ZSM-48 more easily; thus, clustering of the molecular sieve MCM-22 or growth of the molecular sieve MCM-22 in the pore canals of ZSM-22, ZSM-23 and ZSM-48 can be avoided;

(5) In a preferred embodiment of the present invention, an auxiliary agent comprising rhenium and/or stannum is added into the catalyst according to the present invention; by introducing the auxiliary agent, the degree of dispersion of the noble metal constituent can be improved, possibly because that the auxiliary agent and the noble metal may form an alloy phase and thereby clustering of the metal element is avoided; thus, the catalyst can provide more active sites, the loaded amount of the active noble metal constituent can be reduced, and the production cost of the catalyst can be decreased;

(6) For paraffin(alkane) isomerization reaction, not only appropriate pore canal structures but also appropriate acid strength and acid amount are required. With the unique pore canal structures and dimensions, the modified composite molecular sieve provided in the present invention not only can inhibit the multi-branched chain paraffin in the reactants to contact with the active acid sites in the catalyst, but also can selectively inhibit a branched chain rearrangement reaction in the isomerization of alkyl carbonium ion intermediate, so as to prevent the formation of double-branched chain or multi-branched chain products that are large in size and tend to crack quickly. However, it is difficult to meet the requirements of the above-mentioned reaction with the acid sites of a single type of molecular sieve, and a conventional modification doesn't have a characteristic of accurately covering non-ideal acid sites. In a preferred embodiment of the present invention, an organic silicon compound with kinetic diameter slightly smaller than the pore diameter of the outer molecular sieve MCM-22 is used, and the treatment time and depth are controlled appropriately, so that the silicon modifier not only cover the acid sites on the surface of the molecular sieve, but also cover the acid sites in the pore canals of the molecular sieve MCM-22 in the outer layer partially or fully; in contrast, since the pore diameter of the molecular sieve in the core part is smaller than the kinetic diameter of the modifier, the modifier can't enter into the pore canals of the molecular sieve in the core part, and the active sites in those pore canals will not be covered. In that way, the raw material with large molecules is difficult to enter into the pore canals of the molecular sieve in the core part, and react at the active sites in those pore canals, so that the pore canals in the core part can't be blocked while the desired reactants and products can diffuse successfully in the larger pore canals of the molecular sieve in the outer layer, and no reaction will happen and no other byproduct will be generated in the diffusion process; in addition, under the shape-selective reaction mechanism, the formation of double-branched chain products that are large in size and tend to crack quickly can be inhibited. Thus, non-selective reactions can be avoided on the surface of the molecular sieve, while the selective reactions in effective pore canals are improved;

(7) Compared with conventional composite molecular sieves, $SiO_2$ is used in replacement of the molecular sieve as a carrier, the modified composite molecular sieve provided in the present invention still can improve the paraffin isomerization performance of the catalyst while reducing the production cost, since the cost of $SiO_2$ is much lower than the preparation cost of the molecular sieve. For example, when such a catalyst is used in the isomerization dewaxing process of lube distillate, the catalyst not only can remarkably improve the yield of liquid product, but also can significantly improve the viscosity index of lube base oil.

DESCRIPTION OF THE DRAWINGS

The accompanying drawings are provided here to facilitate further understanding on the present invention, and constitute a part of this document. They are used in conjunction with the following embodiments to explain the present invention, but shall not be comprehended as constituting any limitation to the present invention. Among the drawings.

DETAILED DESCRIPTION OF THE EMBODIMENTS

Figure 1:
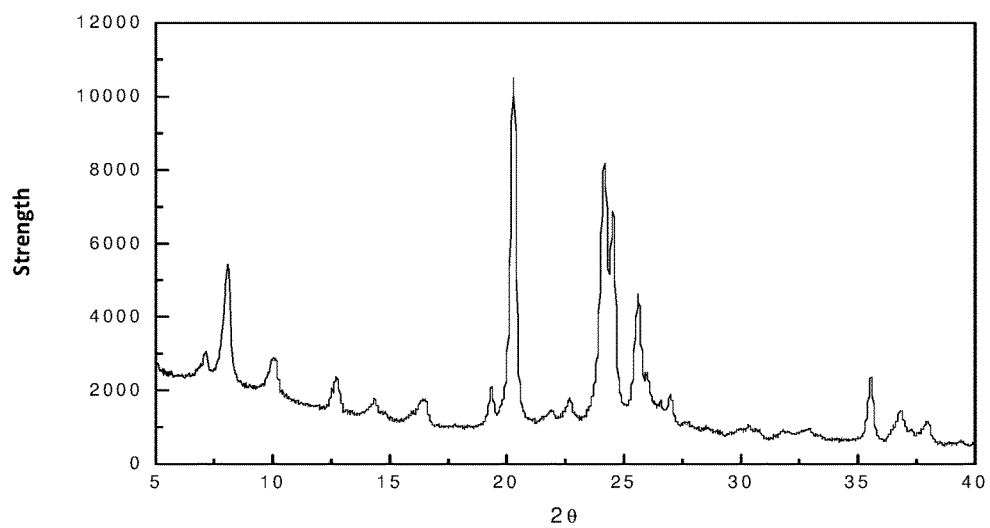
FIGS. 1 and 2 show X-ray diffraction spectrograms of the MCM-22/ZSM-48 molecular sieve prepared in example 1 before and after modification.

Hereunder some embodiments of the present invention will be detailed. It should be appreciated that the embodiments described here are only provided to describe and explain the present invention, but shall not be deemed as constituting any limitation to the present invention.

The ends points and any value in the ranges disclosed in the present invention are not limited to the exact ranges or values. Instead, those ranges or values shall be comprehended as encompassing values that are close to those ranges or values. For numeric ranges, the end points of the ranges, the end points of the ranges and the discrete point values, and the discrete point values can be combined to obtain one or more new numeric ranges, which shall be deemed as having been disclosed specifically in this document.

In the present invention, the modified composite molecular sieve comprises loaded $SiO_2$ and a composite molecular sieve, wherein, the $SiO_2$ is an additive loaded onto the composite molecular sieve by modification. It is known to those skilled in the art that a composite molecular sieve comprises silica polyhedrons; namely, though the composite molecular sieve contains oxygen and silicon, it can't be deemed as containing $SiO_2$. Hence, in the following text, the amount of $SiO_2$ only refers to the amount of the additive $SiO_2$ loaded onto the composite molecular sieve by modification, excluding the silicon and oxygen content in the composite molecular sieve.

As described above, the present invention provides a modified composite molecular sieve, comprising $SiO_2$ and a composite molecular sieve that comprises molecular sieve MCM-22 and molecular sieve A selected from at least one of molecular sieves ZSM-22, ZSM-23 and ZSM-48, wherein, the molecular sieve MCM-22 covers (or grows) around the molecular sieve A, and the $SiO_2$ is loaded on the composite molecular sieve.

According to the present invention, the modification refers to obtain the composite molecular sieve by chemical modification rather than simple physical mixing.

According to the present invention, preferably, the $SiO_2$ and the composite molecular sieve are combined via chemical bonds.

In the molecular sieve according to the present invention, based on the total weight of the final modified composite molecular sieve,
the weight percentage of the loaded $SiO_2$ is 0.1-10%, preferably is 0.5%~8%, preferably is 1%~6%, more preferably is 2%~5%;
the weight percentage of the molecular sieve MCM-22 is 5~30%, preferably is 8~20%, more preferably is 10~15%; and the weight percentage of the molecular sieve A is 55~95%, preferably is 65~90%, more preferably is 75~90%. With the preferred weight percentages described above, the paraffin isomerization performance of the molecular sieve as a carrier can be further improved.

According to the present invention, the weight percentage of the loaded $SiO_2$ in the modified composite molecular sieve is calculated on the basis of the feeds by weight.

In the molecular sieve according to the present invention, the physical and chemical properties of the modified composite molecular sieve include: the content of Bronsted acid is 0.6 $mmol·g^{-1}$~1.2 $mmol·g^{-1}$; preferably the content of Bronsted acid is 0.8 $mmol·g^{-1}$~1.0 $mmol·g^{-1}$.

In the molecular sieve according to the present invention, the physical and chemical properties of the modified composite molecular sieve include: the content of Lewis acid is 0.4 $mmol·g^{-1}$~1.0 $mmol·g^{-1}$; preferably the content of Lewis acid is 0.5 $mmol·g^{-1}$~0.8 $mmol·g^{-1}$.

In the molecular sieve according to the present invention, the physical and chemical properties of the modified composite molecular sieve include: the percentage of strong acids with desorption temperature higher than 450° C. is 15% or higher, preferably the percentage of strong acids with desorption temperature higher than 450° C. is 15~25%.

In the present invention, when the solid acid amount and acid strength distribution of the strong acids or weak acids is characterized through ammonia adsorption-desorption, the ammonia amount absorbed per unit mass (usually 1 g) of sample is used as the total acid amount of the sample; during desorption, as the temperature rises, the ammonia absorbed at the acid sites of the sample will be desorbed gradually; specifically, the ammonia at weak acid sites is desorbed at lower temperatures, since the interaction between the weak acid sites and ammonia is relatively weak; the ammonia at strong acid sites usually is desorbed at higher temperatures, since the interaction between the strong acid sites and ammonia is relatively strong. Usually, acids with desorption temperature higher than 450° C. are referred to as strong acids, and the percentage of strong acids refers to the percentage of the amount of acids with desorption temperature higher than 450° C. to the total acid amount in the sample; in the $NH_3$-TPD spectrum, the percentage of strong acids refers to the percentage of the area of ammonia desorption peaks higher than 450° C. to the total area of desorption peaks.

In the molecular sieve according to the present invention, the physical and chemical properties of the modified composite molecular sieve include: the BET specific surface area is 200~350 m²/g, and the pore volume is 0.3~0.6 ml/g; preferably the BET specific surface area is 200~300 m²/g, and the pore volume is 0.3~0.5 ml/g.

The above physical and chemical properties further prove: after silicon modification, the crystallinity of the molecular sieves in the composite molecular sieve provided in the present invention remains unchanged essentially (the relatively crystallinity is 95% or higher), the BET specific surface area is not changed greatly, but the pore volume is obviously decreased, and the acidity and acid strength distribution are changed obviously, specifically, the Bronsted acid content is decreased by 20%~40%, and the Lewis acid content is decreased by 30%~50%. After the modification, the properties of the composite molecular sieve are as follows: the percentage of strong acid with desorption temperature higher than 450° C. is not higher than 5%; the BET specific surface area is 200~350 m²/g; the pore volume is 0.2~0.5 ml/g; the content of Bronsted acid is 0.36 mmol·g$^{-1}$~0.96 mmol·g$^{-1}$; the content of Lewis acid is 0.2 mmol·g$^{-1}$~0.7 mmol·g$^{-1}$; preferably, the BET specific surface area is 200~300 m²/g, the pore volume is 0.2~0.4 ml/g, the content of Bronsted acid is 0.48 mmol·g$^{-1}$~0.8 mmol·g$^{-1}$; the content of Lewis acid is 0.25 mmol·g$^{-1}$~0.756 mmol·g$^{-1}$.

In the molecular sieve according to the present invention, preferably the molecular sieve A is molecular sieve ZSM-22 and/or ZSM-48, more preferably is ZSM-48.

According to the present invention, there is no special requirement for the method for preparing the molecular sieve, as long as the molecular sieve has the properties described above. However, for the purpose of the present invention, preferably the method for preparing the modified composite molecular sieve comprises: loading an organic silicon source onto a composite molecular sieve optionally in the presence of solvent, and then treating in the presence of water vapor, and optionally drying and/or calcinating, wherein, the composite molecular sieve comprises molecular sieve MCM-22 and molecular sieve A selected from at least one of ZSM-22, ZSM-23 and ZSM-48, and the molecular sieve MCM-22 covers(or grows) around the molecular sieve A.

In the present invention, the loading process refers to a process in which a liquid is loaded on a solid; namely, the loading process in the present invention is a process in which the liquid organic silicon source contacts with the composite molecular sieve.

According to the present invention, the loading process may utilize an impregnation method or a kneading method, preferably is an impregnation method. For example, a solution containing the organic silicon source is prepared for impregnation, wherein, the solvent may be alcohol and/or ether, preferably is methanol or ethanol. To ensure that the weight percentage of the $SiO_2$ in the modified composite molecular sieve is 0.5%-8%, preferably, based on the weight of the modified composite molecular sieve, the loaded amount of the organic silicon source (calculated in $SiO_2$) is 0.1%-10%, preferably is 0.5%~5%, and the impregnation time is 1 h~10 h, preferably is 3 h~6 h.

In the method according to the present invention, the organic silicon source may be any silicon-containing compound that can form $SiO_2$ under hydrolytic condensation reaction conditions. Specifically, the organic silicon source may be selected from one or more of silicon-containing compounds represented by the following formula:

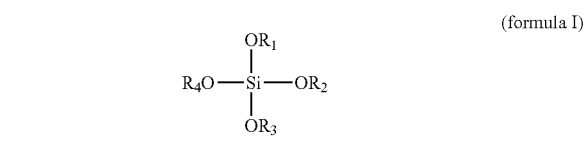

(formula I)

in the formula I, $R_1$, $R_2$, $R_3$ and $R_4$ are a C1-C4 alkyl respectively, including C1-C4 linear-chain alkyl and C3-C4 branched-chain alkyl; for example, $R_1$, $R_2$, $R_3$ and $R_4$ may be methyl, ethyl, n-propyl, isopropyl, n-butyl, sec-butyl, isobutyl, or tert-butyl respectively.

Specifically, the organic silicon source may be one or more of tetramethyl orthosilicate, tetraethyl orthosilicate, tetra-n-propyl orthosilicate, and tetra-n-butyl orthosilicate. In some examples of the present invention, tetraethyl orthosilicate or tetramethyl orthosilicate is used.

According to the present invention, preferably the organic silicon source and the composite molecular sieve are dosed so that the weight percentage of the $SiO_2$ is 0.1-10%, preferably is 0.5%-8%, more preferably is 1%~6%, even more preferably is 2%~5%, based on the total weight of the final modified composite molecular sieve; The weight percentage of the molecular sieve MCM-22 is 5~30%, preferably is 8~20%, more preferably is 10~15%, based on the total weight of the final modified composite molecular sieve; The weight percentage of the molecular sieve A is 55~95%, preferably is 65~90%, more preferably is 75~90%, based on the total weight of the final modified composite molecular sieve.

In the method according to the present invention, preferably the organic silicon source is loaded onto the composite molecular sieve by impregnation, wherein, the impregnation time is 1-10 h, preferably is 3-6 h.

In the preparation method according to the present invention, preferably the organic silicon source is loaded onto the composite molecular sieve in the presence of a solvent, which preferably is alcohol and/or ether, more preferably is alcohol, even more preferably is C1-C5 alcohol, particularly preferably is methanol and/or ethanol.

In the preparation method according to the present invention, more preferably, the mass ratio of the solvent to the organic silicon source is 0.01-0.1:1.

In the preparation method according to the present invention, preferably the treatment conditions include: treating in 100% water vapor.

In the preparation method according to the present invention, preferably the treatment conditions include: the pressure is 0.1 MPa-5.0 MPa, preferably is 0.5 MPa-3.0 MPa.

In the preparation method according to the present invention, preferably the treatment conditions include: the temperature is 100° C.~500° C., preferably is 150° C.~350° C.

In the preparation method according to the present invention, preferably the treatment conditions include: the time is 0.5 h~5 h, preferably is 1.0 h~3.0 h.

Namely, the modification with $SiO_2$ in the present invention is mainly accomplished by high-temperature water vapor treatment.

In a preferred embodiment of the present invention, the preparation steps of the composite molecular sieve include: mixing the molecular sieve A, an optional halogen compound, and silica-alumina gel, and then treating by hydrothermal crystallization, wherein, the silica-alumina gel is obtained by hydrolyzing a mixture of a silicon source, an aluminum source, an alkali source, and an organic template agent for preparing the molecular sieve MCM-22.

In a preferred embodiment of the present invention, the molar composition of the silica-alumina gel is: $Al_2O_3/SiO_2=0.01~0.05$, $OH^-/SiO_2=0.01~0.35$, $R/SiO_2=0.15~1.0$, $H_2O/SiO_2=5~50$; preferably: $Al_2O_3/SiO_2=0.02~0.04$, $OH^-/SiO_2=0.05~0.25$, $R/SiO_2=0.25~0.7$, $H_2O/SiO_2=10~40$, where, R is the organic template agent.

In a preferred embodiment of the present invention, the molar ratio of the added amount of the halogen compound to the amount of $SiO_2$ in the silica-alumina gel is 0.03~0.5, preferably is 0.05~0.3. In the present invention, the halogen compound may be selected in a wide range; preferably, the halogen compound is one or more of C1-C3 organic halogen compounds, more preferably is one or more of $CH_3I$, $CH_3CHCl_2$, and $CHCl_3$.

In a preferred embodiment of the present invention, preferably, the added amount of the molecular sieve A is 0.5~20 of the weight of the $SiO_2$ in the silica-alumina gel, preferably is 1~15.

In the present invention, the silicon source, aluminum source, and alkali source may be compounds commonly used in molecular sieve synthesis.

In a preferred embodiment of the present invention, the silicon source is one or more of silica gel, silica sol, and sodium silicate.

In a preferred embodiment of the present invention, the aluminum source is one or more of sodium metaaluminate, aluminum hydroxide, and active aluminum oxide.

In a preferred embodiment of the present invention, the alkali source is sodium hydroxide and/or potassium hydroxide.

The organic template agent may be selected in a wide range, as long as the organic template agent can be used to prepare the molecular sieve MCM-22. In a preferred embodiment of the present invention, the organic template agent is dimethylene imine or a mixed template agent obtained by mixing dimethylene imine with one or more of hydrocarbon, organic amine, alcohol, and ketone.

In a preferred embodiment of the present invention, the hydrothermal crystallization conditions include: crystallization under self-generated pressure; the crystallization temperature is 100° C.~200° C., preferably is 110° C.~150° C.; the crystallization time is 16 h~120 h, preferably is 20 h~70 h.

The present invention further provides an application of the modified composite molecular sieve provided in the present invention as a catalyst carrier.

The present invention further provides a catalyst that comprises a carrier and a noble metal loaded on the carrier, wherein, the carrier comprises a modified composite molecular sieve that is the modified composite molecular sieve provided in the present invention or the modified composite molecular sieve obtained with the method provided in the present invention.

In a preferred embodiment of the present invention, measured in weight percentage, the weight percentage of the modified composite molecular sieve in the catalyst is 10~90%, preferably is 20%-80%, more preferably is 40%-60%; the weight percentage of the noble metal calculated in the metal element is 0.05%-1.0%, preferably is 0.1%-0.8%, more preferably is 0.2%-0.6%.

In a preferred embodiment of the present invention, the catalyst further comprises an auxiliary agent(catalytic promoter) loaded on the carrier, and the auxiliary agent preferably comprises rhenium and/or stannum, and, measured in weight percentage, the weight percentage of the auxiliary agent calculated in the metal element is 0.1%-10%, preferably is 0.5%-5%, more preferably is 1%-3%.

In a preferred embodiment of the present invention, in the carrier, the weight percentage of the modified composite molecular sieve is 20 wt % or higher, preferably is 50-80 wt %.

In a preferred embodiment of the present invention, the carrier further comprises an inorganic refractory oxide, which is selected from one or more of aluminum oxide, titanium oxide, silicon oxide, boron oxide, magnesium oxide, zirconium oxide, and clay, preferably is aluminum oxide and/or silicon oxide, more preferably is aluminum oxide.

In a preferred embodiment of the present invention, the noble metal is VIII noble metal, preferably is platinum and/or palladium, optimally is platinum.

In the present invention, there is no special requirement for the method for preparing the catalyst, as long as the catalyst has the above-mentioned properties. For example, a noble metal source and an optional auxiliary agent source may be loaded onto the carrier, and then the material is dried and caclined.

In an embodiment of the present invention, the method for preparing the catalyst comprises:

(1) mixing the modified composite molecular sieve with an inorganic refractory oxide source to prepare a catalyst carrier;

(2) loading a noble metal source and an optional auxiliary agent source onto the catalyst carrier prepared in the step (1), and then drying and calcinating.

In the present invention, the inorganic refractory oxide source is an inorganic refractory oxide and/or a precursor of the inorganic refractory oxide; the inorganic refractory oxide may be selected conventionally in the art; for example, the inorganic refractory oxide may be selected from one or more of aluminum oxide, titanium oxide, silicon oxide, boron oxide, magnesium oxide, zirconium oxide, and clay, preferably is aluminum oxide and/or silicon oxide, more preferably is aluminum oxide. The precursor of the inorganic refractory oxide may be selected from one or more of pseudo-boehmite, diaspore, hysrargillite, and bayerite, preferably is pseudo-boehmite, for example.

In the present invention, the noble metal source may be selected conventionally in the art. For example, it may be an oxide of noble metal or a salt of noble metal, etc. For example, it may be chloroplatinic acid, platinum-ammonium coordination compound, palladium-ammonium coordination compound(complex), palladium nitrate, or palladium chloride, etc.

In the present invention, the auxiliary agent source may be selected conventionally in the art. For example, it may be an oxide that comprises the auxiliary agent element or a salt that contains the auxiliary agent element, etc. For example, it may be perrhenic acid, tin tetrachloride, or tin dichloride, etc.

In the catalyst preparation process in the present invention, the loading process may be an impregnation process or ion-exchange process, preferably is an impregnation process. In the impregnation process, the noble metal source and auxiliary agent source may be impregnated in steps or at the same time. Common impregnation solutions usually are water solutions that contain soluble active metal compounds (i.e., a water-soluble noble metal source), and water solutions that contain optional water-soluble auxiliary agent sources, such as chloroplatinic acid solution, platinum-ammonium coordination compound solution, palladium-ammonium coordination compound solution, palladium nitrate solution, palladium chloride solution, and their organic coordination compound solutions, etc.

In a preferred embodiment of the present invention, the present invention provides a paraffin hydroisomerization catalyst, wherein, measured in weight percentage, the weight percentage of modified MCM-22/ZSM-48 composite molecular sieve is 10~90%, preferably is 20%-80%; the weight percentage of VIII noble metal is 0.05%-1.0%, preferably is 0.1%-0.8%; the weight percentage of rhenium and/or stannum auxiliary agent calculated in the metal element is 0.1%-10%, preferably is 0.5%-5.0%; wherein, the modified MCM-22/ZSM-48 composite molecular sieve comprises 0.1%-10 wt % $SiO_2$, preferably 0.5%-5 wt % $SiO_2$ (excluding the silicon oxide in the MCM-22/ZSM-48 composite molecular sieve), and the MCM-22/ZSM-48 composite molecular sieve accounts for the remaining weight percentage; in the MCM-22/ZSM-48 composite molecular sieve, the molecular sieve MCM-22 grows (or covers) around the molecular sieve ZSM-48, and the weight percentage of the MCM-22 is 1.0~50 wt %, preferably is 5.0~30 wt %.

The catalyst provided in the present invention comprises an inorganic refractory oxide, which is selected from one or more of aluminum oxide, titanium oxide, silicon oxide, boron oxide, magnesium oxide, kaolin, and clay, preferably is aluminum oxide and/or kaolin, more preferably is aluminum oxide.

The properties of the catalyst provided in the present invention are as follows: the BET specific surface area is 200~350 $m^2/g$, and the pore volume is 0.3~0.5 ml/g. The specific surface area and pore volume of the catalyst provided in the present invention are obtained by measuring with a low-temperature liquid nitrogen adsorption method with a ASAP2400 unit and calculating through BET calculation.

The present invention provides a method for preparing a paraffin hydroisomerization catalyst, comprising the following steps:

1) preparing MCM-22/ZSM-48 composite molecular sieve;
2) loading tetraethyl orthosilicate onto the above-mentioned molecular sieve, treating by high-temperature water vapor treatment, and drying and calcinating, so as to obtain a modified MCM-22/ZSM-48 composite molecular sieve;
3) mixing the modified composite molecular sieve prepared in the step (2) with an inorganic refractory oxide to prepare a catalyst carrier; and
4) loading VIII noble metal and an auxiliary agent onto the catalyst carrier prepared in the step (3), and then drying and calcinating, so as to obtain the catalyst provided in the present invention.

In the method provided in the present invention, the MCM-22/ZSM-48 composite molecular sieve is prepared in the step (1) through the following procedure: adding molecular sieve ZSM-48 into a silica-alumina gel, wherein, the molar composition of the silica-alumina gel is: $Al_2O_3/SiO_2=0.01~0.05$, $OH^-/SiO_2=0.02~0.35$, $R/SiO_2=0.15~1.0$, $H_2O/SiO_2=5~50$, the molar ratio of the halogen compound to $SiO_2=0.03~0.5$, where, R is an organic template agent. Preferably, $Al_2O_3/SiO_2=0.02~0.04$, $OH^-/SiO_2=0.01~0.10$, $R/SiO_2=0.25~0.7$, $H_2O/SiO_2=10~40$, and the molar ratio of the halogen compound to $SiO_2=0.05~0.3$.

The organic template agent R may be dimethylene imine or a mixed template agent formed by mixing dimethylene imine with one or more of hydrocarbon, organic amine, alcohol and ketone.

The halogen compound is one or more of C1-C3 organic halogen compounds, such as $CH_3I$, $CH_3CHCl_2$, and $CHCl_3$, etc.

The silicon source, aluminum source, and alkali source are compounds commonly used in molecular sieve synthesis. For example, the silicon source is silica gel, silica sol, or sodium silicate, etc.; the aluminum source is sodium metaaluminate, aluminum hydroxide, active aluminum oxide, or aluminate, etc.; the alkali source is sodium hydroxide or potassium hydroxide, etc.

The added amount of the molecular sieve ZSM-48 is 0.5~20 of the weight of the $SiO_2$ (calculated in silica in the silica-alumina gel), preferably is 1.0~15.

Crystallization is carried out under self-generated pressure, wherein, the crystallization temperature is 100° C.~200° C., preferably is 110° C.~150° C.; the crystallization time is 16 h-120 h, preferably is 20 h-70 h; thus, the composite molecular sieve is obtained.

The MCM-22/ZSM-48 composite molecular sieve in the step 2) is modified with tetraethyl orthosilicate modifier; the loading method may be an impregnation method or kneading method, preferably is an impregnation method; organic alcoholate or ether may be used to prepare a solution that contains tetraethyl orthosilicate, preferably methanol or ethanol is used.

Based on the weight of the modified composite molecular sieve, the loaded amount of the tetraethyl orthosilicate (calculated in $SiO_2$) is 0.1%-10%, preferably is 0.5%~5%; the impregnation time is 1 h-10 h, preferably is 3 h-6 h; after tetraethyl orthosilicate impregnation, the composite molecular sieve is treated by high-temperature water vapor treatment at 100%, under the following conditions: the treatment pressure is 0.1 MPa-5.0 MPa, preferably is 0.5 MPa-3.0 MPa; the treatment temperature is 100° C.~500° C., preferably is 150° C.~350° C.; the treatment time is 0.5 h-5 h, preferably is 1.0 h-3.0 h.

The inorganic refractory oxide in the step 3) is selected from one or more of aluminum oxide, titanium oxide, silicon oxide, boron oxide, magnesium oxide, zirconium oxide, and clay, preferably is aluminum oxide and/or silicon oxide, more preferably is aluminum oxide. The precursor of the inorganic refractory oxide may be selected from one or more of pseudo-boehmite, diaspore, hysrargillite, and bayerite, preferably is pseudo-boehmite.

The VIII noble element in the step 4) preferably is platinum and/or palladium, optimally is platinum. The noble metal and the auxiliary agent may be added into the catalyst through an impregnation process or ion-exchange process, preferably through an impregnation process. The impregnation of them may be carried out in steps or at the same time. Common active constituent impregnation solutions are water solutions that contain soluble active metal compounds, such as chloroplatinic acid solution, platinum-ammonium coordination compound solution, palladium-ammonium coordination compound solution, palladium nitrate solution, palladium chloride solution, and their organic coordination compound solutions, etc.; the auxiliary agent that contains rhenium is perrhenic acid; and the auxiliary agent that contains stannum is tin tetrachloride or tin dichloride solution.

The catalyst provided in the present invention is applicable to the isomerization treatment process of different waxy raw materials, which may be waxy raw materials with initial boiling point equal to or higher than 140° C., such as diesel oil, white oil, atmospheric heavy distillate (AGO), reduced pressure distillate (VGO), hydrocracking tail oil, lube oil, or paraffin, etc. The catalyst is particularly suitable for use in the treatment process of lube oil. Usually, waxy raw materials that have high contents of impurities such as sulfur and nitrogen have to be hydro-refined before the isomerization treatment can be made. The conditions of shape-selective isomerization reaction of paraffin in the crude lube stock are: 2 MPa-20 MPa hydrogen pressure, 260° C.~400° C. temperature, 0.5 $h^{-1}$~4.0 $h^{-1}$ volumetric space velocity, and 200~1,000 hydrogen-to-oil volume ratio; preferably, the conditions are: 5 MPa-10 MPa hydrogen pressure, 320° C.~380° C. temperature, 1.0 $h^{-1}$~3.0 $h^{-1}$ volumetric space velocity, and 300~500 hydrogen-to-oil volume ratio.

The present invention provides a MCM-22/ZSM-22 composite molecular sieve catalyst, which comprises modified MCM-22/ZSM-22 composite molecular sieve and VIII noble metal active constituent, wherein, based on the weight percentage of the catalyst, the weight percentage of the modified MCM-22/ZSM-22 composite molecular sieve is 10~90%, preferably is 20%-80%; the weight percentage of the VIII noble metal is 0.1%-1.5%; wherein, the weight percentage of $SiO_2$ in the modified MCM-22/ZSM-22 composite molecular sieve is 0.1%-10%, preferably is 0.5%-5% (excluding the $SiO_2$ in the MCM-22/ZSM-22 composite molecular sieve), and the inorganic refractory oxide accounts for the remaining weight percentage; in the MCM-22/ZSM-22 composite molecular sieve, the molecular sieve MCM-22 wraps(grows) around the molecular sieve ZSM-22, and the weight percentage of the molecular sieve MCM-22 in the MCM-22/ZSM-22 composite molecular sieve is 1.0~50%, preferably is 5.0~30%.

The catalyst provided in the present invention comprises an inorganic refractory oxide, which is selected from one or more of aluminum oxide, titanium oxide, silicon oxide, boron oxide, magnesium oxide, zirconium oxide, and clay, preferably is aluminum oxide and/or silicon oxide, more preferably is aluminum oxide. The precursor of the inorganic refractory oxide may be selected from one or more of pseudo-boehmite, diaspore, hysrargillite, and bayerite, preferably is pseudo-boehmite.

The properties of the catalyst provided in the present invention are as follows: the BET specific surface area is 200~350 $m^2/g$, and the pore volume is 0.3~0.5 ml/g. The specific surface area and pore volume of the catalyst provided in the present invention are obtained by measuring with a low-temperature liquid nitrogen adsorption method with a ASAP2400 unit and calculating through BET calculation.

The term "paraffin" also can be called hydrocarbon alkyl or alkane in the present invention.

The present invention provides a method for preparing a paraffin hydroisomerization catalyst, comprising the following steps:
1) preparing MCM-22/ZSM-22 composite molecular sieve;
2) loading tetraethyl orthosilicate onto the above-mentioned molecular sieve, treating by high-temperature water vapor treatment, and drying and calcinating, so as to obtain a modified MCM-22/ZSM-22 composite molecular sieve;
3) mixing the composite molecular sieve prepared in the step 2) with an inorganic refractory oxide to prepare a catalyst carrier; and
4) loading the VIII noble active metal constituent onto the carrier through a conventional impregnation process, and then drying and calcinating, so as to obtain the catalyst finally.

In the method provided in the present invention, the MCM-22/ZSM-22 composite molecular sieve is prepared in the step 1) through the following procedure: adding molecular sieve ZSM-22 into a silica-alumina gel, wherein, the molar composition of the silica-alumina gel is: $Al_2O_3/SiO_2$=0.01~0.05, $OH^-/SiO_2$=0.02~0.35, $R/SiO_2$=0.15~1.0, $H_2O/SiO_2$=5~50, the molar ratio of the halogen compound to $SiO_2$=0.03~0.5, where, R is an organic template agent. Preferably, $Al_2O_3/SiO_2$=0.02~0.04, $OH^-/SiO_2$=0.01~0.10, $R/SiO_2$=0.25~0.7, $H_2O/SiO_2$=10~40, and the molar ratio of the halogen compound to $SiO_2$=0.05~0.3. The organic template agent R may be dimethylene imine or a mixed template agent formed by mixing dimethylene imine with one or more of hydrocarbon, organic amine, alcohol and ketone. The halogen compound is one or more of C1-C3 organic halogen compounds, such as $CH_3I$, $CH_3CHCl_2$, and $CHCl_3$, etc. The silicon source, aluminum source, and alkali source are compounds commonly used in molecular sieve synthesis. For example, the silicon source is silica gel, silica sol, or sodium silicate, etc.; the aluminum source is sodium metaaluminate, aluminum hydroxide, active aluminum oxide, or aluminate, etc.; the alkali source is sodium hydroxide or potassium hydroxide, etc. The added amount of the molecular sieve ZSM-22 is 0.5~20 of the weight of the $SiO_2$ (calculated in silicon in the silica-alumina gel), preferably is 1.0~15. Crystallization is carried out under self-generated pressure, wherein, the crystallization temperature is 100° C.~200° C., preferably is 110° C.~150° C.; the crystallization time is 16 h-120 h, preferably is 20 h-70 h; thus, the composite molecular sieve is obtained.

The MCM-22/ZSM-22 composite molecular sieve in the step 2) is modified with tetraethyl orthosilicate modifier; the loading method may be an impregnation method or kneading method, preferably is an impregnation method; organic alcoholate or ether may be used to prepare a solution that contains tetraethyl orthosilicate, preferably methanol or ethanol is used. Based on the weight of the molecular sieve, the loaded amount of the tetraethyl orthosilicate (calculated in $SiO_2$) is 0.1%-10%, preferably is 0.5%-5%; the impregnation time is 1 h-10 h, preferably is 3 h-6 h; after tetraethyl orthosilicate impregnation, the composite molecular sieve is treated by high-temperature water vapor treatment at 100%, under the following conditions: the treatment pressure is 0.1 MPa-5.0 MPa, preferably is 0.5 MPa-3.0 MPa; the treatment temperature is 100° C.~500° C., preferably is 150° C.~350° C.; the treatment time is 0.5 h-5 h, preferably is 1.0 h-3.0 h.

The inorganic refractory oxide in the step 3) is selected from one or more of aluminum oxide, titanium oxide, silicon oxide, boron oxide, magnesium oxide, zirconium oxide, and clay, preferably is aluminum oxide and/or silicon oxide, more preferably is aluminum oxide. The precursor of the inorganic refractory oxide may be selected from one or more of pseudo-boehmite, diaspore, hysrargillite, and bayerite, preferably is pseudo-boehmite.

The VIII noble element in the step 4) preferably is platinum and/or palladium, optimally is platinum. Utilizing a metallic acid, metallic acid salt(Metallate), chloride, amino complex, hydroxo complex or VIII noble metal, or a mixture of them as a raw material, the noble metal and the composite molecular sieve are combined through a process comprising impregnation, precipitation, deposition, binder bonding, or mechanical stitching. etc.

The catalyst provided in the present invention is applicable to the isomerization treatment process of different waxy raw materials, which may be waxy raw materials with initial boiling point equal to or higher than 140° C., such as diesel oil, white oil, atmospheric heavy distillate (AGO), reduced pressure distillate (VGO), hydrocracking tail oil, lube oil, or paraffin, etc. The catalyst is particularly suitable for the treatment process of lube oil. Usually, waxy raw materials that have high contents of impurities such as sulfur and nitrogen have to be hydro-refined before the isomerization treatment can be made. The conditions of shape-selective isomerization reaction of paraffin in the crude lube stock are: 2 MPa-20 MPa hydrogen pressure, 260° C.~400° C. temperature, 0.5 $h^{-1}$~4.0 $h^{-1}$ volumetric space velocity, and 200~1,000 hydrogen-to-oil volume ratio; preferably, the conditions are: 5 MPa-10 MPa hydrogen pressure, 320° C.~380° C. temperature, 1.0 $h^{-1}$~3.0 $h^{-1}$ volumetric space velocity, and 300~500 hydrogen-to-oil volume ratio.

The present invention provides an application of the catalyst provided in the present invention in paraffin isomerization.

The catalyst provided in the present invention is applicable to the isomerization treatment process of different waxy raw materials, which may be waxy raw materials with initial boiling point equal to or higher than 140° C., such as one or more of diesel oil, white oil, atmospheric heavy distillate (AGO), reduced pressure distillate (VGO), hydrocracking tail oil, lube oil, or paraffin, etc. The catalyst is particularly suitable for use in the treatment process of lube oil. Usually, waxy raw materials that have high contents of impurities such as sulfur and nitrogen have to be hydro-refined before the isomerization treatment can be made.

In the application according to the present invention, preferably the operating conditions include: 2 MPa-20 MPa hydrogen pressure, 260° C.~400° C. temperature, 0.5 $h^{-1}$~4 $h^{-1}$ volumetric space velocity, and 200~1,000 hydrogen-to-oil volume ratio; preferably: 5 MPa-10 MPa hydrogen pressure, 320° C.~380° C. temperature, 1 $h^{-1}$~3 $h^{-1}$ volumetric space velocity, and 300~500 hydrogen-to-oil volume ratio.

In a preferred embodiment of the present invention, the raw material for paraffin isomerization is lube oil, and the operating conditions include: 2 MPa-20 MPa hydrogen pressure, 260° C.~400° C. temperature, 0.5 $h^{-1}$~4.0 $h^{-1}$ volumetric space velocity, and 200~1,000 hydrogen-to-oil volume ratio; preferably, the conditions are: 5 MPa-10 MPa hydrogen pressure, 320° C.~380° C. temperature, 1.0 $h^{-1}$~3.0 $h^{-1}$ volumetric space velocity, and 300~500 hydrogen-to-oil volume ratio.

Hereunder the preparation process of the catalyst provided in the present invention will be further detailed in examples, but the present invention is not limited to these examples. In the following examples or comparative examples, unless otherwise specified, the contents are weight percentages. The specific surface area and pore volume of the catalyst provided in the present invention are obtained by measuring with a low-temperature liquid nitrogen adsorption method with a ASAP2405 unit and calculating through BET calculation. The $NH_3$-TPD of the catalyst provided in the present invention is measured on a MICRO MERITICS 2910 BET unit, the area of the desorption peaks in the $NH_3$-TPD spectrum represents the acid concentration on the sample surface, and the desorption temperature represent the acid strength in the sample. The Py-IR acidity of the catalyst provided in the present invention is measured with a Nicolet Magna-IR 560 infrared spectrometer, the absorption peak at 1,540 $cm^{-1}$ is regarded as the characteristic absorption peak of Bronsted acid, the adsorption peak at 1,450 $cm^{-1}$ is regarded as the characteristic absorption peak of Lewis acid, and then the acid amount and acid strength distribution of Bronsted acid and Lewis acid are calculated respectively.

Example 1

1.488 g $NaAlO_2$ and 36.06 g sodium hydroxide solution are mixed in a 500 mL stainless steel reactor to a homogeneous state, 23 g silica gel, 3.3 g$CHCl_3$, 359.3 g deionized water, and 3.00 g hexamethylene imine (HMI) are added into the reactor in sequence while stirring, and finally 100 g ZSM-48 is added. The mixture is stirred further for 10 min., then the reactor is sealed, and crystallization is carried out at 130° C. for 20 h. After the crystallization is finished, the solid product (MCM-22/ZSM-48) is separated from the product, and numbered as MS-1, wherein, the weight percentage of MCM-22 is 11.1%, and the X-ray diffraction spectrogram is shown in FIG. 1. It can be seen from FIG. 1: the molecular sieve MS-1 is a MCM-22/ZSM-48 composite molecular sieve; the analysis of physical and chemical properties is shown in Table 1.

Figure 2:
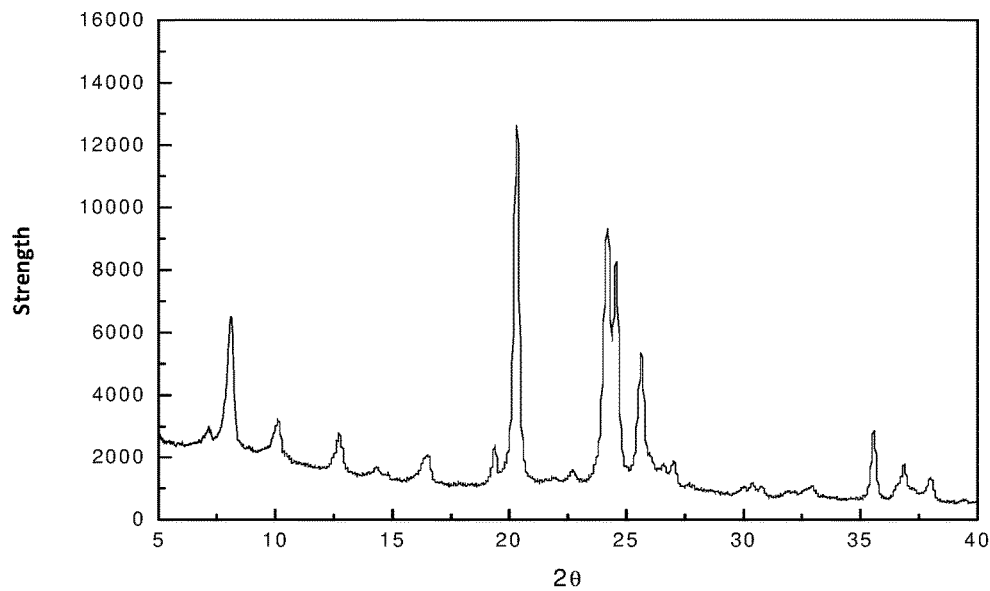

16.8 g tetraethyl orthosilicate is prepared into 150 g methanol solution of tetraethyl orthosilicate, 100 g above-mentioned MCM-22/ZSM-48 molecular sieve is impregnated in the solution for 2.5 h, and then the MCM-22/ZSM-48 molecular sieve is treated in 100% high-temperature water vapor under the following conditions: 1.5 MPa treatment pressure, 350° C. treatment temperature, and 2.0 h treatment time. Thus, a modified MCM-22/ZSM-48 composite molecular sieve with 4.8% loaded amount of $SiO_2$, and is numbered as S-1. The X-ray diffraction spectrogram is shown in FIG. 2. It can be seen from FIG. 2: The crystalline phase of the modified molecular sieve MS-1 remains unchanged, indicating that the entire modification process has no influence on the crystalline structure of the composite molecular sieve. The analysis of physical and chemical properties is shown in Table 1.

Example 2

Figure 3:
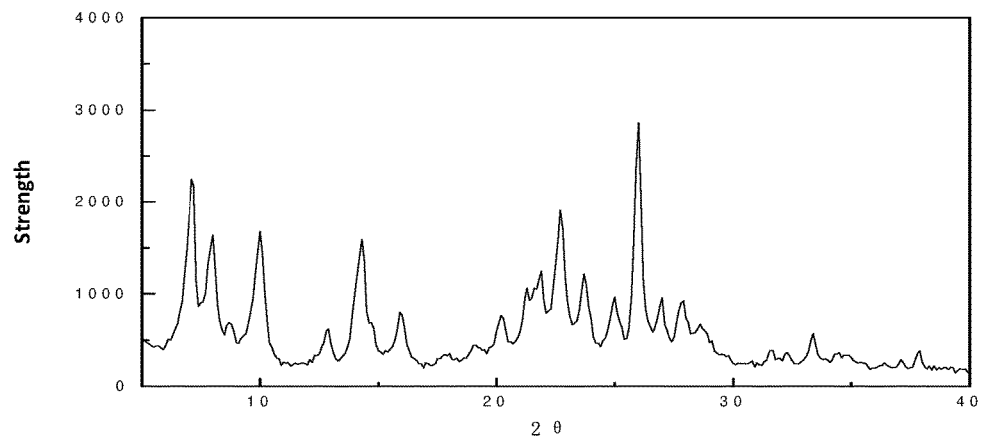
FIG. 3 shows an X-ray diffraction spectrogram of the MCM-22/ZSM-22 molecular sieve prepared in example 3.

4.26 g $NaAlO_2$ and 19.08 g sodium hydroxide solution are mixed in a 500 mL stainless steel reactor to a homogeneous state, 33 g silica gel, 408.2 g deionized water, and 18.96 g hexamethylene imine (HMI) are added into the reactor in sequence while stirring, then 1.65 g $CH_3I$ is added, and finally 55 g ZSM-48 is added. The mixture is stirred further for 10 min., then the reactor is sealed, and crystallization is carried out at 120° C. for 15 h. After the crystallization is finished, the solid product (MCM-22/ZSM-48) is separated from the product, and numbered as MS-2, wherein, the weight percentage of MCM-22 is 25.4%, and the X-ray diffraction spectrogram is shown in FIG. 3. It can be seen from FIG. 3: the molecular sieve MS-2 is a MCM-22/ZSM-48 composite molecular sieve; the analysis of the physical and chemical properties is shown in Table 1.

5.5 g tetraethyl orthosilicate is prepared into 150 g methanol solution of tetraethyl orthosilicate, 100 g above-mentioned MCM-22/ZSM-48 molecular sieve is impregnated in the solution for 6.5 h, and then the MCM-22/ZSM-48 molecular sieve is treated in 100% high-temperature water vapor under the following conditions: 1.0 MPa treatment pressure, 350° C. treatment temperature, and 3.5 h treatment time. Thus, a modified MCM-22/ZSM-48 composite molecular sieve with 1.5% loaded amount of $SiO_2$, and is numbered as S-2. The X-ray diffraction spectrogram is similar to that shown in FIG. 2; the analysis of the physical and chemical properties is shown in Table 1.

Example 3

Figure 4:
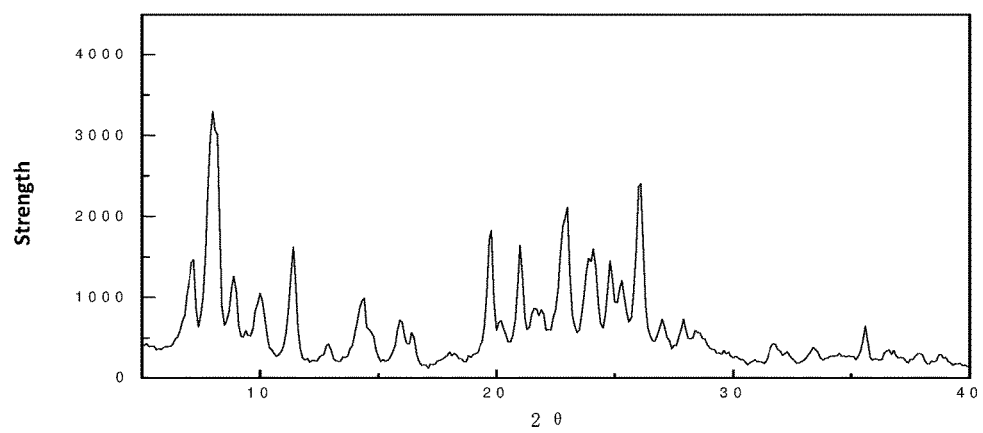
FIG. 4 shows an X-ray diffraction spectrogram of the MCM-23/ZSM-22 molecular sieve prepared in example 4.

1.136 g $NaAlO_2$ and 24.04 g sodium hydroxide solution are mixed in a 500 mL stainless steel reactor to a homogeneous state, 22 g silica gel, 237 g deionized water, 12 g HMI, and 6 g cyclohexane are added into the reactor in sequence while stirring, and finally 120 g ZSM-22 is added. The mixture is stirred further for 10 min., then the reactor is sealed, and crystallization is carried out at 120° C. for 15 h. After the crystallization is finished, the solid product (MCM-22/ZSM-22) is separated from the product, and numbered as MS-3, wherein, the weight percentage of MCM-22 is 7.5%, and the X-ray diffraction spectrogram is shown in FIG. 4. It can be seen from FIG. 4: the molecular sieve MS-3 is a MCM-22/ZSM-22 composite molecular sieve; the analysis of the physical and chemical properties is shown in Table 1.

10.8 g tetraethyl orthosilicate is prepared into 150 g methanol solution of tetraethyl orthosilicate, 100 g above-mentioned MCM-22/ZSM-22 molecular sieve is impregnated in the solution for 6.5 h, and then the MCM-22/ZSM-22 molecular sieve is treated in 100% high-temperature water vapor under the following conditions: 1.5 MPa treatment pressure, 350° C. treatment temperature, and 4.0 h treatment time. Thus, a modified MCM-22/ZSM-22 composite molecular sieve with 3.1% loaded amount of $SiO_2$, and is numbered as S-3. The X-ray diffraction spectrogram is similar to that shown in FIG. 2; the analysis of the physical and chemical properties is shown in Table 1.

Example 4

The MCM-22/ZSM-23 composite molecular sieve is prepared through a process identical to the process used in the example 1, but 150 g molecular sieve ZSM-23 is added; thus, a modified MCM-22/ZSM-23 composite molecular sieve with 1.1% loaded amount of $SiO_2$ is obtained, and numbered as S-4, wherein, the weight percentage of the MCM-22 is 8.32%; the X-ray diffraction spectrogram is similar to that shown in FIG. 2; the analysis of the physical and chemical properties of S-4 before and after the modification is shown in Table 1.

Example 5

The MCM-22/ZSM-48 composite molecular sieve is prepared through a process identical to the process used in the example 1, but the loaded amount of $SiO_2$ in the obtained modified MCM-22/ZSM-48 composite molecular sieve is 2.8%; the modified MCM-22/ZSM-48 composite molecular sieve is numbered as S-5; the X-ray Diffraction spectrogram is similar to that shown in FIG. 2; the analysis of the physical and chemical properties is shown in Table 1.

Example 6

The modified composite molecular sieve is prepared with the method used in the example 1, but an ethanol solution of tetraethyl orthosilicate is used; the other conditions are the same as those used in the example 1. A MCM-22/ZSM-48 composite molecular sieve is obtained, and numbered as S-6; the X-ray diffraction spectrogram is similar to that shown in FIG. 2; the analysis of the physical and chemical properties is shown in Table 1.

Example 7

The modified composite molecular sieve is prepared with the method used in the example 1, but tetra-n-butyl orthosilicate is used in replacement of tetraethyl orthosilicate; the other conditions are the same as those used in the example 1. A MCM-22/ZSM-48 composite molecular sieve is obtained, and numbered as S-7; the X-ray diffraction spectrogram is similar to that shown in FIG. 2; the analysis of the physical and chemical properties is shown in Table 1.

Comparative Example 1

A molecular sieve ZSM-48 is synthesized with the method disclosed in the Patent Application No. 201110217576.X.

The preparation process is as follows: 5.0 g sodium hydroxide and 2.0 g sodium aluminate are dissolved in 300 ml deionized water; then, 15 g 1,6-dibromo-hexane, 24 g trimethylamine, and 45 g ethanol are added at room temperature while stirring; the mixture is stirred further for 0.5 h, and then 55 g white carbon black is added; next, the mixture is stirred for 1.0 h, and then moved into an air-tight stainless steel reactor. Crystallization is carried out at 160° C. for 6 days; thus, a crystallized product is obtained; then, the product is cooled, and the solid is separated from the mother liquid by centrifugal separation; next, the obtained sample is dried in air at 100° C. for 8 h; thus, molecular sieve ZSM-48 powder is obtained, and is numbered as Z-1.

Comparative Example 2

A molecular sieve MCM-22 is synthesized with the method disclosed in the U.S. Pat. No. 4,954,325.

The preparation process is as follows: 0.71 g $NaAlO_2$ and 3.18 g sodium hydroxide solution are mixed in a 100 mL stainless steel reactor to a homogeneous state, 5.5 g silica gel, 69.7 g deionized water, and 3.16 g hexamethylene imine (HMI, 99%) are added into the reactor in sequence while stirring, wherein, the molar composition of the reaction mixture is: $SiO_2/Al_2O_3=30$, $H_2O/SiO_2=45$, $HMI/SiO_2=0.35$, and $Na_2O/SiO_2=0.11$. The mixture is stirred further for 10 min., then the reactor is sealed, and crystallization is carried out at 110° C. for 60 h. After the crystallization is finished, the solid product is separated, and the obtained sample is dried in air at 100° C. for 8 h; thus, molecular sieve MCM-22 powder is obtained, and numbered as Z-2.

Comparative Example 3

A molecular sieve ZSM-48 (prepared with the method described in the comparative example 1) and molecular sieve MCM-22 (prepared with the method described in the comparative example 2) are used, and mixed mechanically at 4:1 (mass ratio); the obtained mixture is numbered as Z-3.

Comparative Example 4

A molecular sieve ZSM-22 (synthesized with the method disclosed in the Patent Application No. 200510066975, through a process detailed as follows) and molecular sieve MCM-22 (prepared with the method described in the comparative example 2) are used, and mixed mechanically at 4:1 (mass ratio).

The preparation process of ZSM-22 is as follows: 3.24 g $NaAlO_2$ is added into a mixture of 4.9 g NaOH and 548 water, the obtained mixture is stirred for 4 h, and then 106 g diethyl triamine is added, and the mixture is stirred for 1 h; finally, 270 g 30% silica gel is added; thus, an initial colloid is obtained. The molar composition of the initial colloid is: $SiO_2/Al_2O_3$=117, $OH/SiO_2$=0.1, $R/SiO_2$=0.8, and $H_2O/SiO_2$=30. The initial colloid is stirred for 12 h, and then moved to a 1,000 mL high pressure reactor; the reactor is sealed, and the stirring speed is adjusted to 300 rpm; next, the reactor is heated up to 180° C. within 4 h, and hydrothermal crystallization is carried out at the temperature for 72 h. After the crystallization is finished, the solid product is separated; thus, a molecular sieve ZSM-22 sample is obtained, and numbered as Z-4.

Comparative Example 5

A molecular sieve ZSM-23 (synthesized with the method disclosed in the Patent Application CN 102897785A, through a process detailed as follows) and molecular sieve MCM-22 (prepared with the method described in the comparative example 2) are used, and mixed mechanically at 4:1 (mass ratio). the BET specific surface area is 287 $m^2/g$, and the pore volume is 0.26 ml/g;

The preparation process of ZSM-23 is as follows: 3 g aluminum hydroxide is mixed with 8.4 g water solution of pyrrolidine (with 70% pyrrolidine content), at a ratio of $R/Al_2O_3$=8 (molar ratio). The mixture is loaded into a crystallization reactor that has a PTFE lining, and is held at 150° C. for reaction for 20 h, the product is cooled to room temperature, and mixed with 40 g silica gel, 81 g deionized water, 8.3 g pyrrolidine, and 2.4 g ZSM-23 intensively. The molar ratio of the obtained mixture is: $SiO_2/Al_2O_3$=65, $H_2O/SiO_2$=7, and $R/SiO_2$=0.3. The mixture is crystallized in a high-pressure reactor at 150° C. for 70 h. After the crystallization is finished, the solid product is separated; thus, a molecular sieve ZSM-23 sample is obtained, and numbered as Z-5.

Comparative Example 6

The molecular sieve is prepared with the method described in the example 1, but the obtained composite molecular sieve is not treated through the follow-up step of modification with tetraethyl orthosilicate. The obtained composite molecular sieve is numbered as Z-6.

Comparative Example 7

The molecular sieve is prepared with the method described in the example 1, but tetraethyl orthosilicate is replaced with silica gel in the step (2). The obtained molecular sieve is numbered as Z-7.

Comparative Example 8

The molecular sieve is prepared with the method described in the example 1, but the composite molecular sieve obtained in the step (1) is directly mixed with tetraethyl orthosilicate, and then the mixture is dried and caclined (under the conditions described in the example 1); the obtained molecular sieve is numbered as Z-8.

Preparation of Catalyst 100 g MCM-22/ZSM-48 molecular sieve prepared in the example 1 is mixed intensively with 100 g aluminum hydroxide (measured in aluminum oxide) (product SB from Condean (a German company)), and then mixed with 10 g sesbania powder to a homogeneous state; next, 230 ml water and 14 ml concentrated nitric acid (at 66.5% mass concentration) are added, and the obtained mixture is kneaded intensively into plastic paste; the plastic paste is extruded on an extruder into cylindrical bars in 1.5 mm diameter; the cylindrical bars are dried at 100° C. for 16 h, and then caclined in air at 550° C. for 4 h; thus, the catalyst carrier described in the present invention is obtained; the catalyst carrier is impregnated with $H_2PtCl_6$ solution that contains perrhenic acid to saturated state with a conventional pore-filling impregnation method; next, the product is dried at 100° C. for 8 h, and caclined in air at 500° C. for 3 h; thus, the catalyst described in the present invention is obtained, and numbered as E-1. The physical and chemical properties of the catalyst are shown in Table 1. The reaction result is shown in Table 3.

Catalysts are prepared through the above-mentioned steps, but the modified composite molecular sieves in the examples 2-7 are used, and the dosage and composition are adjusted accordingly; thus, catalysts (E-2)~(E-7) are obtained. The physical and chemical properties of the catalysts are shown in Table 1, and the reaction results are shown in Table 3.

Catalysts are prepared through the above-mentioned steps, but the molecular sieves in the comparative examples 1-8 are used, and the dosage and composition are adjusted accordingly; thus, catalysts (C-1)~(C-8) are obtained. The physical and chemical properties of the catalysts are shown in Table 1, and the reaction results are shown in Table 3.

TABLE 1

Main Physical and Chemical Properties of the Molecular Sieves

| Molecular sieve | Before Modification | | | | | | After Modification | | | | | |
|---|---|---|---|---|---|---|---|---|---|---|---|---|
| | MCM-22①, % | S, $m^2/g$ | V, ml/g | mmol·$g^{-1}$ $C_B$ | $C_L$ | Percentage of Strong Acids >450° C., % | $SiO_2$, % | S, $m^2/g$ | V, ml/g | mmol·$g^{-1}$ $C_B$ | $C_L$ | Percentage of Strong Acids >450° C., % |
| S-1 | 11.1 | 260 | 0.35 | 0.93 | 0.74 | 16.3 | 4.8 | 250 | 0.32 | 0.64 | 0.45 | 2.5 |
| S-2 | 25.4 | 249 | 0.37 | 0.81 | 0.65 | 13.3 | 1.5 | 245 | 0.33 | 0.57 | 0.39 | 4.0 |
| S-3 | 7.50 | 258 | 0.38 | 1.06 | 0.82 | 20.3 | 3.1 | 260 | 0.33 | 0.74 | 0.49 | 3.1 |

TABLE 1-continued

Main Physical and Chemical Properties of the Molecular Sieves

| Molecular sieve | Before Modification | | | | | | After Modification | | | | | |
|---|---|---|---|---|---|---|---|---|---|---|---|---|
| | MCM-22[1], % | S, $m^2/g$ | V, ml/g | $C_B$ mmol·$g^{-1}$ | $C_L$ | Percentage of Strong Acids >450° C., % | $SiO_2$, % | S, $m^2/g$ | V, ml/g | $C_B$ mmol·$g^{-1}$ | $C_L$ | Percentage of Strong Acids >450° C., % |
| S-4 | 8.32 | 257 | 0.34 | 1.13 | 0.92 | 24.3 | 1.1 | 260 | 0.30 | 0.74 | 0.56 | 3.8 |
| S-5 | 11.1 | 260 | 0.35 | 0.93 | 0.74 | 16.3 | 2.8 | 264 | 0.31 | 0.7 | 0.51 | 3.5 |
| S-6 | 11.1 | 260 | 0.35 | 0.93 | 0.74 | 16.3 | 4.8 | 257 | 0.33 | 0.69 | 0.48 | 2.8 |
| S-7 | 11.1 | 260 | 0.35 | 0.93 | 0.74 | 16.3 | 4.8 | 261 | 0.30 | 0.60 | 0.41 | 2.9 |
| Z-6 | 11.1 | 260 | 0.35 | 0.93 | 0.74 | 16.3 | 0 | — | — | — | — | — |
| Z-7 | 11.1 | 260 | 0.35 | 0.93 | 0.74 | 16.3 | 4.8 | 240 | 0.30 | 0.41 | 0.21 | 1.7 |
| Z-8 | 11.1 | 260 | 0.35 | 0.93 | 0.74 | 16.3 | 4.8 | 257 | 0.25 | 0.35 | 0.17 | 1.1 |

Note:
(1) [1] is based on the mass of the composite molecular sieve;
(2) S represents specific surface area, V represents pore volume;
(3) CB and CL represent Bronsted acid amount and Lewis acid amount respectively;
(4) distribution of acids >450° C.

TABLE 2

Main Constituents of Catalysts

| Catalyst | Modified Molecular Sieve[1], % | Pt, wt % | Pd, wt % | Auxiliary Agent, % |
|---|---|---|---|---|
| E-1 | S-1/50.0 | 0.33 | — | 0.8[5] |
| E-2 | S-2/50.0 | 0.61 | — | 1.2[5] |
| E-3 | S-3/50.0 | — | 0.8 | 1.5[6] |
| E-4 | S-4/30.0 | 0.56 | — | 2.3[5] |
| E-5 | S-5/60.0 | 0.43 | — | 3.8[6] |
| E6 | S-6/50.0 | 0.33 | — | 0.8[5] |
| E7 | S-7/50.0 | 0.33 | — | 0.8[5] |
| C-1 | Z-1/50.0 | 0.33 | — | 0.8[5] |
| C-2 | Z-2/50.0 | 0.33 | — | 0.8[5] |
| C-3 | Z-3[2]/50.0 | 0.33 | — | 0.8[5] |
| C-4 | Z-4[3]/50.0 | 0.33 | — | 0.8[5] |
| C-5 | Z-5[4]/50.0 | 0.33 | — | 0.8[5] |
| C-6 | Z-6/50.0 | 0.33 | — | 0.8[5] |
| C-7 | Z-7/50.0 | 0.33 | — | 0.8[5] |
| C-8 | Z-8/50.0 | 0.33 | — | 0.8[5] |

Note:
(1) [1] is based on the mass of the catalyst;
[2] represents ZSM-48/MCM-22 composite molecular sieve;
[3] represents ZSM-22/MCM-22 composite molecular sieve;
[4] represents ZSM-23/MCM-22 composite molecular sieve;
[5] auxiliary agent rhenium;
[6] auxiliary agent stannum

Test Cases

The catalysts prepared in the above examples and comparative examples are evaluated in a 200 ml medium-size fixed bed-type reactor respectively, wherein, the loaded amount of catalyst is 200 ml, the catalyst is pre-reduced before it is fed into the reactor, so that the noble metal in the catalyst is converted into a reduced state; the reducing conditions are as follows: In the presence of hydrogen, 300° C.~500° C. temperature, 0.5 MPa~10 MPa pressure, and 1~12 h time; the processing conditions for the evaluation are: pressure: 9 MPa, volumetric space velocity: 1.0 $h^{-1}$, and hydrogen-to-oil volume ratio: 800. The main properties of the raw oil used for the evaluation are shown in Table 3.

TABLE 3

Main Properties of Raw Oil

| | |
|---|---|
| Sulfur, μg/g | 4.1 |
| Nitrogen, μg/g | 1.0 |
| Viscosity (@50° C.), $mm/s^2$ | 30.78 |
| Pour point, ° C. | 40 |
| Wax content, wt % | 38.8 |
| Distillation range, ° C. (D1160) | |
| IBP/10% | 404/419 |
| 30%/50% | 426/436 |
| 70%/90% | 456/495 |
| 95%/EBP | 511/530 |

The catalyst provided in the present invention has advantages of high yield, low pour point (solidifying point), and high viscosity index of the product, when the catalyst is applied in the isomerization dewaxing process of lube oil.

TABLE 4

Catalyst Evaluation Conditions and Results

| Catalyst No. | E-1 | E-2 | E-3 | E-4 | E-5 | E-6 | E-7 | C-1 | C-2 | C-3 | C-4 | C-5 | C-6 | C-7 | C-8 |
|---|---|---|---|---|---|---|---|---|---|---|---|---|---|---|---|
| Reaction temperature, ° C. | 325 | 330 | 330 | 335 | 320 | 330 | 335 | 325 | 325 | 330 | 332 | 335 | 325 | 350 | 355 |
| $C_5^+$ liquid yield, wt % | 97.5 | 97.1 | 96.0 | 96.3 | 95.8 | 95.1 | 94.3 | 84.6 | 71.1 | 88.9 | 92.2 | 91.3 | 75.3 | 76.1 | 75.3 |
| Yield of lube base oil, wt % | 84.5 | 83.6 | 82.1 | 82.2 | 82.4 | 81.3 | 81.2 | 60.3 | 44.0 | 73.6 | 75.2 | 74.1 | 50.8 | 45.8 | 47.6 |
| Properties of Lube Base Oil | | | | | | | | | | | | | | | |
| Viscosity index | 128 | 127 | 124 | 125 | 123 | 121 | 120 | 105 | 101 | 105 | 108 | 107 | 105 | 107 | 104 |
| Pour point, ° C. | −21 | −22 | −21 | −20 | −22 | −21 | −21 | −21 | −20 | −21 | −22 | −21 | −21 | −20 | −19 |

It can be seen from the evaluation result in Table 4: compared with the catalysts in the comparative examples, when the catalyst provided in the present invention is used in the hydro-treatment process of lube distillate, on the premise of similar pour point of lube base oil, the $C_5^+$ liquid yield can be increased by 3.5 wt % or more, the yield of lube base oil can be increased by 8 wt % or more, the viscosity index of the product can be improved by 10~24 units, which indicate that the catalyst provided in the present invention attains a remarkably improved effect when it is used in the treatment process of crude lube stock.

The invention claimed is:

1. A modified composite molecular sieve, comprising:
   $SiO_2$ and a composite molecular sieve that comprises molecular sieve MCM-22 and a crystalline molecular sieve selected from at least one of ZSM-22, ZSM-23 and ZSM-48, wherein, the molecular sieve MCM-22 covers around the crystalline molecular sieve, and the $SiO_2$ is loaded on the composite molecular sieve.

2. The modified composite molecular sieve according to claim 1, wherein, a weight percentage of the loaded $SiO_2$ is 0.1-10%;
   a weight percentage of the molecular sieve MCM-22 is 5 to 30%; and
   a weight percentage of the crystalline molecular sieve is 55 to 95%, based on a total weight of the modified composite molecular sieve.

3. The modified composite molecular sieve according to claim 2, wherein, the weight percentage of the loaded $SiO_2$ is 1-6%;
   the weight percentage of the molecular sieve MCM-22 is 8 to 20%; and
   the weight percentage of the crystalline molecular sieve is 75 to 90%.

4. The modified composite molecular sieve according to claim 1, wherein the composite molecular sieve has properties chosen from one or more of
   a content of Bronsted acid of 0.6 mmol·$g^{-1}$ to 1.2 mmol·$g^{-1}$,
   a content of Lewis acid of 0.4 mmol·$g^{-1}$ to 1.0 mmol·$g^{-1}$,
   a percentage of strong acids with desorption temperature higher than 450° C. of 15% or higher,
   a BET specific surface area of 200 $m^2$/g to 350 $m^2$/g,
   or a pore volume of 0.3 $m^2$/g to 0.6 ml/g.

5. The modified composite molecular sieve according to claim 1, wherein
   the modified composite molecular sieve has one or more of properties chosen from a
   content of Bronsted acid of 0.8 mmol·$g^{-1}$ to 1.0 mmol·$g^{-1}$,
   a content of Lewis acid of 0.5 mmol·$g^{-1}$ to 0.8 mmol·$g^{-1}$,
   a percentage of strong acids with desorption temperature higher than 450° C. of 15% to 25%
   BET specific surface area is 200 $m^2$/g to 300 $m^2$/g,
   or a pore volume is 0.3 ml/g to 0.5 ml/g.

6. The modified composite molecular sieve according to claim 1, wherein the crystalline molecular sieve is ZSM-22, ZSM-48, or a combination thereof.

7. A method for preparing a modified composite molecular sieve of claim 1, comprising: loading an organic silicon source onto a composite molecular sieve optionally in the presence of a solvent, and then treating in the presence of water vapor, and optionally drying and/or calcinating, wherein, the composite molecular sieve comprises molecular sieve MCM-22 and crystalline molecular sieve selected from at least one of ZSM-22, ZSM-23 and ZSM-48, and the molecular sieve MCM-22 covers around the crystalline molecular sieve.

8. The preparation method according to claim 7, wherein the organic silicon source is selected from one or more of silicon-containing compounds represented by formula I

(formula I)

wherein $R_1$, $R_2$, $R_3$ and $R_4$ are independently a C1-C4 alkyl,
wherein the organic silicon source and the composite molecular sieve are added so that a weight percentage of the $SiO_2$ is 0.1% to 10%,
a weight percentage of the molecular sieve MCM-22 is 5% to 30%,
and a weight percentage of the crystalline molecular sieve is 55% to 95%, based on a total weight of the modified composite molecular sieve.

9. The preparation method according to claim 8, wherein, $R_1$, $R_2$, $R_3$ and $R_4$ are independently chosen from methyl, ethyl, n-propyl, isopropyl, n-butyl, sec-butyl, isobutyl, or tert-butyl,
the organic silicon source and the composite molecular sieve are dosed so that the weight percentage of the $SiO_2$ is 1% to 6%,
the weight percentage of the molecular sieve MCM-22 is 8% to 20%, and
the weight percentage of the crystalline molecular sieve is 75% to 90%.

10. The preparation method according to claim 7, wherein the solvent an alcohol, an ether, or a combination thereof, and a mass ratio of the solvent to the organic silicon source is (0.01-0.1):1.

11. The preparation method according to claim 7, wherein, in the loading step,
the organic silicon source is loaded on the composite molecular sieve by impregnation, and the impregnation time is 1-10 h, wherein, in the treatment step,
the treatment is carried out
in 100% water vapor under a pressure of 0.1 MPa to 5 MPa at a temperature of 100° C. to 500° C. for a duration of 0.5 h to 5 h.

12. The preparation method according to claim 7, wherein preparation of the composite molecular sieve comprises: mixing the crystalline molecular sieve, an optional halogen compound, and silica-alumina gel to form a mixture, and then treating the mixture by hydrothermal crystallization, wherein the silica-alumina gel is obtained by hydrolyzing a mixture of a silicon source, an aluminum source, an alkali source, and an organic template agent for preparing the molecular sieve MCM-22.

13. The preparation method according to claim 12, wherein
a molar composition of the silica-alumina gel comprises $Al_2O_3/SiO_2$=0.01 to 0.05, $OH^-/SiO_2$=0.01 to 0.35, $R/SiO_2$=0.15 to 1.0, and $H_2O/SiO_2$=5 to 50, wherein R is the organic template agent, and
a molar ratio of the halogen compound to $SiO_2$ in the silica-alumina gel is 0.03 to 0.5, and the halogen compound is one or more chosen from $CH_3I$, $CH_3CHCl_2$, or $CHCl_3$.

14. The preparation method according to claim 12, wherein an added amount of the crystalline molecular sieve is 0.5 to 20 of the weight of $SiO_2$ in the silica-alumina gel.

15. The preparation method according to claim 12, wherein
the silicon source is one or more of silica gel, silica sol, and sodium silicate,
the aluminum source is one or more chosen from sodium metaaluminate, aluminum hydroxide, or active aluminum oxide,
the alkali source is sodium hydroxide, potassium hydroxide, or a mixture thereof,
the organic template agent is dimethylene imine or a mixed template agent formed by mixing dimethylene imine with one or more chosen from a hydrocarbon, an organic amine, an alcohol, or a ketone.

16. The preparation method according to claim 12, wherein the hydrothermal crystallization is carried out under self-generated pressure at a temperature of 100° C. to 200° C. for a duration of 16 h to 120 h.

17. An paraffin isomerization catalyst comprising a carrier and a noble metal loaded on the carrier, wherein the carrier comprises a modified composite molecular sieve of claim 1.

18. The catalyst according to claim 17, wherein, based on a total weight of the catalyst, a weight percentage of the modified composite molecular sieve in the catalyst is 10% to 90% and a weight percentage of the noble metal calculated in the metal element is 0.05% to 1.0%.

19. The catalyst according to claim 17, wherein the catalyst further comprises:
an auxiliary agent loaded on the carrier, wherein the auxiliary agent comprises one or more metals chosen from rhenium, stannum, or both, and, a weight percentage of the one or more metals in the auxiliary agent is 0.1% to 10% of a total weight of the catalyst; and
the carrier further comprises an inorganic refractory oxide selected from one or more of aluminum oxide, titanium oxide, silicon oxide, boron oxide, magnesium oxide, zirconium oxide, and clay.

20. The catalyst according to claim 17, wherein the noble metal is a VIII noble metal.

* * * * *